United States Patent
Hynes

(10) Patent No.: US 7,887,566 B2
(45) Date of Patent: Feb. 15, 2011

(54) INTERVERTEBRAL SUPPORT DEVICE WITH BIAS ADJUSTMENT AND RELATED METHODS

(76) Inventor: Richard A. Hynes, 603 Atlantic St., Melbourne Beach, FL (US) 32951

( * ) Notice: Subject to any disclaimer, the term of this patent is extended or adjusted under 35 U.S.C. 154(b) by 756 days.

(21) Appl. No.: 11/226,148

(22) Filed: Sep. 14, 2005

(65) Prior Publication Data
US 2006/0058792 A1 Mar. 16, 2006

Related U.S. Application Data

(60) Provisional application No. 60/610,496, filed on Sep. 16, 2004.

(51) Int. Cl.
*A61B 17/70* (2006.01)
(52) U.S. Cl. .................................. 606/254
(58) Field of Classification Search ............. 606/254, 606/257, 261, 71, 282; 623/17.11–17.16
See application file for complete search history.

(56) References Cited

U.S. PATENT DOCUMENTS

| | | | | |
|---|---|---|---|---|
| 4,078,559 A * | 3/1978 | Nissinen | ...................... | 606/258 |
| 4,112,935 A * | 9/1978 | Latypov et al. | ................ | 606/54 |
| 4,484,570 A | 11/1984 | Sutter et al. | ................ | 128/92 D |
| 5,360,430 A | 11/1994 | Lin | .............................. | 606/61 |
| 5,375,823 A | 12/1994 | Navas | ........................ | 267/195 |
| 5,415,661 A | 5/1995 | Holmes | ........................ | 606/69 |
| 5,423,816 A | 6/1995 | Lin | .............................. | 606/61 |
| 5,562,737 A | 10/1996 | Graf | .............................. | 623/17 |
| 5,569,251 A | 10/1996 | Baker et al. | ..................... | 606/69 |
| 5,609,634 A | 3/1997 | Voydeville | ................... | 623/17 |
| 5,616,142 A | 4/1997 | Yuan et al. | ..................... | 606/61 |
| 5,672,175 A * | 9/1997 | Martin | ...................... | 606/86 A |
| 5,702,443 A | 12/1997 | Brånemark | ................... | 623/11 |
| 5,704,936 A | 1/1998 | Mazel | ........................ | 606/61 |
| 5,725,582 A | 3/1998 | Bevan et al. | ................... | 623/17 |
| 5,800,433 A | 9/1998 | Benzel et al. | ................. | 606/61 |
| RE36,221 E | 6/1999 | Breard et al. | ................. | 606/61 |
| 5,961,516 A | 10/1999 | Graf | ............................. | 606/61 |
| 6,093,188 A * | 7/2000 | Murray | ........................ | 606/282 |
| 6,129,728 A | 10/2000 | Schumacher et al. | ........... | 606/71 |
| 6,136,002 A | 10/2000 | Shih et al. | ...................... | 606/61 |
| 6,241,730 B1 | 6/2001 | Alby | ............................. | 606/61 |
| 6,267,764 B1 | 7/2001 | Elberg | ........................ | 606/61 |

(Continued)

FOREIGN PATENT DOCUMENTS

FR 2709246 2/1994

(Continued)

*Primary Examiner*—Thomas C Barrett
*Assistant Examiner*—Michael J Araj
(74) *Attorney, Agent, or Firm*—Allen, Dyer, Doppelt, Milbrath & Gilchrist, P.A.

(57) ABSTRACT

An intervertebral support device may include upper and lower vertebral mounting fixtures to be respectively connected to an upper and a lower vertebra in a patient's spine. The device may further include a bias member for urging the upper and lower vertebral mounting fixtures together, and a bias adjuster connected to the bias member maintained in tension for adjusting the tension thereof. The bias adjuster advantageously allows a spinal surgeon installing the intervertebral support device to adjust the tension of the bias member during installation, as well as to re-adjust the tension post-operatively during follow-up visits to modify a patient's intervertebral mobility as needed.

12 Claims, 4 Drawing Sheets

U.S. PATENT DOCUMENTS

| | | | |
|---|---|---|---|
| 6,402,750 B1 * | 6/2002 | Atkinson et al. | 606/279 |
| 6,440,169 B1 * | 8/2002 | Elberg et al. | 623/17.16 |
| 6,565,576 B1 * | 5/2003 | Stauch et al. | 606/71 |
| 2003/0130661 A1 | 7/2003 | Osman | 606/71 |
| 2004/0030395 A1 * | 2/2004 | Blunn et al. | 606/61 |
| 2004/0073215 A1 | 4/2004 | Carli | 606/61 |
| 2005/0043732 A1 * | 2/2005 | Dalton | 606/61 |
| 2005/0102028 A1 * | 5/2005 | Arnin et al. | 623/17.13 |
| 2006/0036240 A1 * | 2/2006 | Colleran et al. | 606/61 |

FOREIGN PATENT DOCUMENTS

| | | |
|---|---|---|
| RU | 2103937 | 2/1998 |
| WO | 2004034916 | 4/2004 |
| WO | WO2005/018419 | 3/2005 |

* cited by examiner

INTERVERTEBRAL SUPPORT DEVICE WITH BIAS ADJUSTMENT AND RELATED METHODS

CROSS-REFERENCE TO RELATED APPLICATIONS

This application claims the benefit of U.S. Provisional Application No. 60/610,496, filed Sep. 16, 2004, which is hereby incorporated herein in its entirety by reference.

FIELD OF THE INVENTION

The present invention relates to the field of medical devices, and, more particularly, to spinal implants and related methods.

BACKGROUND OF THE INVENTION

Spinal implant devices are commonly used to correct or stabilize the position of vertebral segments in a patient's back. Such correction may be necessary as a result of accidents, degenerative diseases, etc.

U.S. Pat. No. Re. 36,221 to Breard et al. discloses an intervertebral stabilizer which includes one or more flexible or semi-elastic ligaments. The stabilizer may be implanted on one side only or on both sides of the spines of the vertebrae concerned, or on the front face or rear face thereof. Screws may be implanted in corresponding vertebrae for retaining the ligament therebetween. Each of the screws may further include a detachable, threaded cap for securing the ligament to the screw.

Another intervertebral stabilizer device for attachment to two vertebrae is disclosed in U.S. Pat. No. 5,375,823 to Navas. This stabilizer includes a housing defining an internal chamber, a piston within the housing, and first and second elastic dampers within the chamber to dampen movement of the piston. The volume and characteristics of these dampers may be varied to provide more or less resistance. Further, the stabilizer also includes a rod extending from each end of the chamber, each of which terminates in a ball joint. A screw is mounted in each of the two vertebrae, and each screw has a head which receives the ball joints and pivots with respect thereto. A stated goal of this device is to relieve an injured disk when it withstands compression and traction forces.

An intervertebral locking device is disclosed in U.S. Pat. No. 5,360,430 to Lin which includes a bottom base, a bracing member, a top base, and at least one adjusting arm. According to one embodiment of the invention, the bracing member may be a spring body made of an elastic material. The locking device may be implanted within the spinal column.

U.S. Pat. No. 5,616,142 to Yuan et al. discloses a vertebral fixation device which includes a receiving piece, a sliding piece, and a plurality of fastening elements for connection of the two. More specifically, the receiving piece is provided with two sliding grooves in which the sliding piece is slidably received.

Furthermore, U.S. Pat. No. 6,136,002 to Shih et al. discloses an anterior spinal fixation system including upper and lower vertebral plates with a pair of parallel rods connected therebetween. More particularly, each vertebral plate includes a staple vertebral plate attached to a respective vertebra by two screws, and a universal cover plate for securing the rods between itself and the staple vertebral plate. The universal cover plates are connected to the staple vertebral plates with locking nuts.

Despite the advantages of such spinal implant devices, further operational and adjustment features may be desirable in certain applications.

SUMMARY OF THE INVENTION

In view of the foregoing background, it is therefore an object of the present invention to provide an intervertebral support device allowing post-operative tension adjustment and related methods.

This and other objects, features, and advantages in accordance with the present invention are provided by an intervertebral support device which may include upper and lower vertebral mounting fixtures to be respectively connected to an upper and a lower vertebra in a patient's spine. The device may further include a bias member maintained in tension for urging the upper and lower vertebral mounting fixtures together, and a bias adjuster connected to the bias member for adjusting the tension thereof. The bias adjuster advantageously allows a spinal surgeon installing the intervertebral support device to adjust the tension of the bias member during installation, as well as to post-operatively re-adjust the tension during follow-up visits to modify a patient's intervertebral mobility as needed.

By way of example, the bias adjuster may be mechanically actuatable with a tool, such as a wrench or screwdriver, through a minimally invasive technique (e.g., percutaneously). In addition, the bias adjuster may be magnetically actuatable as well as electrically actuatable, so that adjustment may be performed externally and remotely. The bias adjuster may also be inductively powered, for example. The bias member may be a spring, for example.

More particularly, the upper and lower vertebral mounting fixtures may each include a respective anchor to be connected to each vertebral pedicle, and a respective cross-support member connected between the anchors. Moreover, the bias member may be connected between the cross-support members and centered between the anchors in a medialized position relative to the spine. Also, the anchors may be pedicle screws.

A method aspect of the invention is for providing intervertebral support for a patient's spine and may include connecting upper and lower vertebral mounting fixtures each to a respective upper and a lower vertebra in the patient's spine. The method may further include connecting a bias member and a bias adjuster between the upper and lower vertebral mounting fixtures. The bias member may be maintained in tension for urging the upper and lower vertebral mounting fixtures together. Also, the tension of the bias member may be adjusted using the bias adjuster.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notation are used to indicate similar elements in alternate embodiments.

Figure 1:
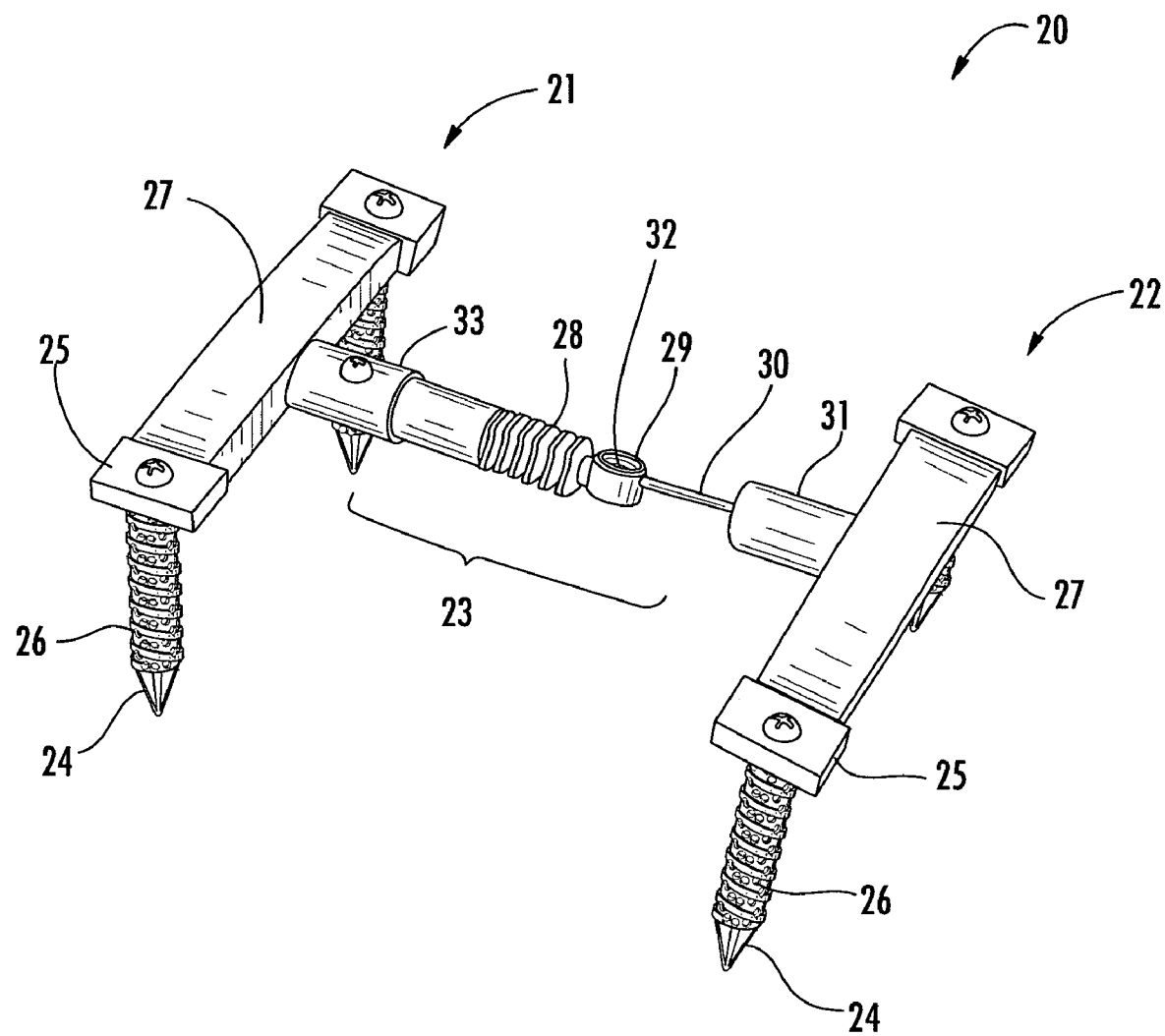
FIG. 1 is a perspective view of an intervertebral support device in accordance with the present invention.
Figure 2:
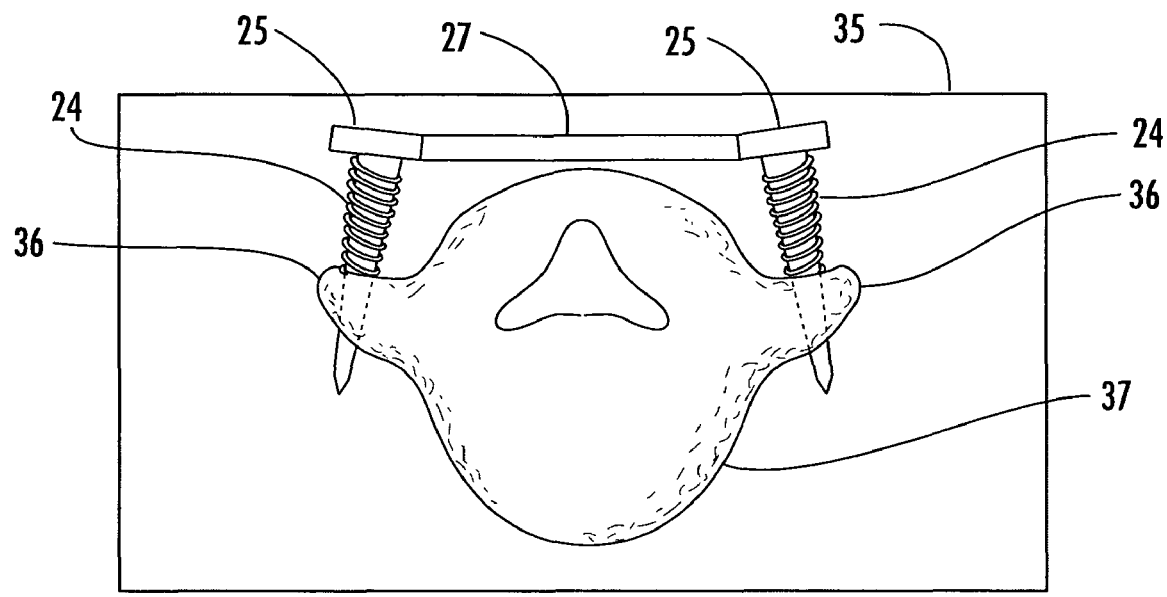
FIG. 2 is a schematic cross-sectional end view of a vertebral mounting fixture of the intervertebral support device of FIG. 1 after implantation.
Figure 3:
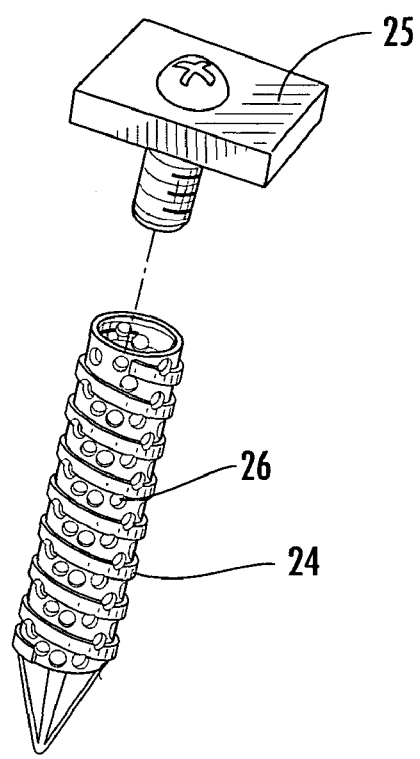
FIG. 3 is a perspective view of a pedicle screw and associated detachable locking head of a vertebral mounting fixture of FIG. 1 shown in greater detail.

Referring initially to FIGS. 1 through 3, a support device 20 for supporting intervertebral disks is first described. Generally speaking, the support device 20 is preferably installed on the posterior or back of a patient's spine to limit spinal movement which may otherwise damage the disk. For example, the device 20 may advantageously be used to support a slipped disk or one that has been damaged by scoliosis to prevent further damage to the disk.

The support device illustratively includes upper and lower vertebral mounting fixtures 21, 22, one of which is to be mounted posteriorly through an incision in a patient's back on an upper vertebra above the problem disk, and the other is to be similarly mounted posteriorly on a lower vertebra below the problem disk. A flexible support structure 23 is connected between the vertebral mounting fixtures 21, 22 and centrally positioned over the spine. The flexible support member 23 allows limited movement of the vertebrae along three coordinate axes to reduce further damage to the problem disk.

Each vertebral mounting fixture 21, 22 illustratively includes a pair of anchors 24 each to be connected on either side of the vertebra, and a detachable locking head 25 to be connected to each of the anchors. In the illustrated embodiment, the anchors 24 are threaded "ingrowth" pedicle screws to be screwed through the pedicles 36 of a vertebra 37, although other suitable anchors may also be used. The illustrated pedicle screws are referred to as ingrowth screws because they are hollow and have holes 26 therein to allow the vertebra 37 to grow into the screw to form a substantially permanent connection therewith, as will be appreciated by those skilled in the art. This is to prevent the screws from "wiggling" lose after repeated movement. As shown in FIG. 3, the detachable locking heads 25 may be connected to the anchors 24 by threads, although other suitable detachable connections and/or anchor arrangements may also be used.

Furthermore, each vertebral mounting fixture 21, 22 further includes a cross-support member 27 releasably connected between the detachable locking heads 25. By way of example, the cross-supports may slidably connect with corresponding recesses in the detachable locking heads (not shown). Further, each detachable locking head 25 may have a relatively low profile to advantageously minimize protrusion from the spine, as opposed to many typical spinal screws which have a raised connector to allow connection to a support rod, for example.

The flexible support member 23 illustratively includes a bias member 28 for urging the upper and lower vertebral mounting fixtures together, and a bias adjuster 29 connected thereto for adjusting a tension of the bias member. The bias adjuster 29 advantageously allows a spinal surgeon installing the intervertebral support device to adjust the tension of the bias member during installation, as well as to post-operatively re-adjust the tension during follow-up visits to modify a patient's intervertebral mobility as needed.

In the illustrated embodiment, the bias member 28 is a spring, and the bias adjuster 29 is a spool. A wire or cable 30 is connected between the spool and an extension 31 carried by the cross-support member 27 of the lower vertebral support fixture 22, although the wire may be connected directly to the cross support member without an intervening bracket. Likewise, the spring is connected to an extension 33 carried by the cross-support member 27 of the upper vertebral support fixture 12, but again may be connected directly to the cross-support member in certain embodiments.

In the illustrated embodiment, the spool has a tool fitting 32 for receiving an adjustment tool, which in the present example is a Phillips screwdriver. Of course, fittings for other suitable tools such as a slot screwdriver, hex head wrench, etc., may also be used. Moreover, such tools may be cannulated to assist with accessing the tool fitting 32, if desired. As the spool is turned to take up the cable 30, the tension of the spring is increased to thereby bias the upper and lower vertebral support fixtures 21, 22 closer together. On the other hand, as the spool is loosened to pay out more of the cable 30, the tension on the spring is reduced, which decreases the biasing force biasing the upper and lower vertebral support fixtures 21, 22 closer together and thus allows a greater degree of movement by the patient.

The bias adjuster 29 may be approached surgically through a minimally invasive technique (e.g., percutaneously). This could be assisted by X-ray, fluoroscopy, navigation systems, etc., for example, in certain applications. While not shown for clarity of illustration, in some embodiments a sleeve may be used to cover the flexible support member 23. By way of example, a cylindrical plastic sleeve with a small opening therein for accessing the tool fitting 32 may be used, although other sleeves or covers may be used in other embodiments.

The flexible support member 23 may include various elements in different embodiments, such as rods, polymers, plates, cushions or dampers, etc., that allow desired movement or restriction of the spine. Moreover, other materials such as hydraulic metal, plastic, polymers or other material may be utilized to provide torsion, bending, distraction or compression in a way that mirrors or mimics the three-dimensional motion of the cervical or lumbar intervertebral disk. It should also be noted that more than one spring, wire, etc. may also be used. Also, other mechanical bias adjusters 29 may also be used to tighten or loosen the flexible support member 23, such as screws, nuts, clamps, pins, etc., as will be appreciated by those skilled in the art.

The motion of the support device 20 preferably mirrors the three planes of motion of the spine. It will be understood by those skilled in the art that the motion of each intradiskal segment in the three planes is relatively small. Therefore, the support device 20 will preferably have a significant torsional strength and require relatively little bending or torsion.

Figure 4:
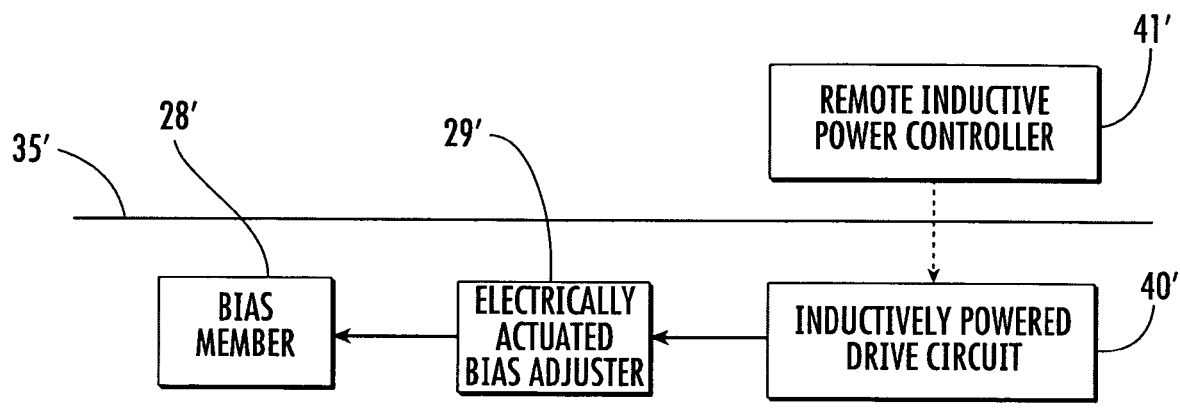
FIGS. 4 and 5 are schematic block diagrams of alternative bias adjustment arrangements for the intervertebral support device of FIG. 1.

Turning now additionally to FIG. 4, an alternate bias adjustment arrangement illustratively includes an electrical drive circuit 40' implanted within the patient for driving the bias adjuster 29' based upon drive signals from a remote controller 41'. By way of example, in such embodiments the bias adjuster 29' may be a small motor. In the illustrated example, the device circuit 40' is inductively powered by the controller 41' so that a power source (i.e., battery) need not be implanted in the patient. However, in some embodiments an implanted power source may be used if proper care is taken to make sure no chemicals or other toxins can be released into the patient's system.

Figure 5:
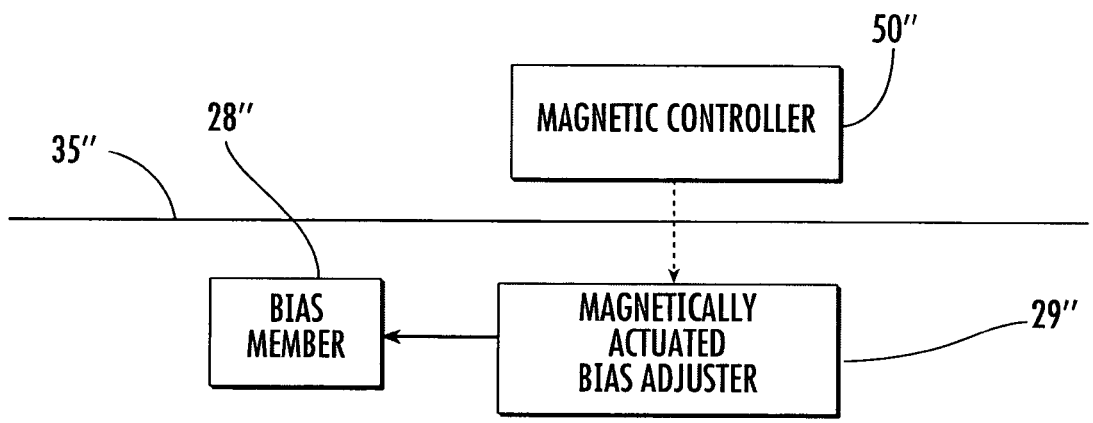

In still another related embodiment now described with reference to FIG. 5, the bias adjuster 29" may be magnetically actuatable by a remote magnetic controller 50", as will be appreciated by those skilled in the art. The embodiments illustrated in FIGS. 4 and 5 advantageously allow bias adjustments to be performed after surgery has been completed and the wound closed without having to perform any further percutaneous procedures on the patient, i.e., no further openings need be made in the patient's skin.

In other embodiments, the bias adjustment may be performed through movements to stiffen or loosen the bias member 28. In addition, external manual manipulation may also be possible to change the tension if the device is placed subcutaneously to allow local pressure to change the tension, as will be appreciated by those skilled in the art.

Because the support device 20 advantageously provides the ability to modulate the tension or movement thereof after implantation, this provides a significant benefit over prior art devices which are merely placed in the patient and cannot be adjusted over time in accordance with the needs of the patient or the type of procedure being performed without further surgery. Moreover, the support device may also be used to provide a fixed fusion or "100% stiff" device percutaneously, or by other adjustment method as discussed above, which also provides a significant advantage over typical prior art devices.

The intervertebral support device 20 advantageously allows normal three-dimensional movement of a spinal disk. The support device 20 may advantageously prevent collapse of the disk, decrease motion of the facets, and closure of the neural foramina, as will be appreciated by those skilled in the art. This will allow normal controlled motion of the disk, preventing transference of stresses to the disks above and below the problem disk, which occurs after a spinal fusion, for example. The support device 20 may also be used to reduce the need for a spinal fusion by allowing preservation of spine motion segments, thus reducing the need for further surgery and stiffness of the spine.

Current treatment for spinal disorders typically involves either decompression and/or stabilization through fusion of the intervertebral disk segments. One downside to such treatment modality is the historical chance of stress transference to the disk above or below the problem disk, resulting in deterioration of the disk or a need for further surgery. A significant benefit of the intervertebral support device 20 is that it can maintain disk motion while preserving disk height, neural foraminal patency, and reducing subluxation. Moreover, it may further prevent or decrease pain, provide support for the spine to permit normal motion, and thereby allow less transference of stress and reduce the need for further surgery.

Another important benefit of the support device 20 is that it is preferably posteriorly implanted, and thus avoids the need for anterior abdominal surgery. However, the support device 20 may also function as an adjunctive stabilizer of an anterior disk replacement placed posteriorly in the spine. It may also be an adjunctive device for use in conjunction with a posterior lumbar interbody fusion technique for replacement of the disk and nuclear material itself with intradiskal prostheses, as will be appreciated by those skilled in the art.

Figure 6:
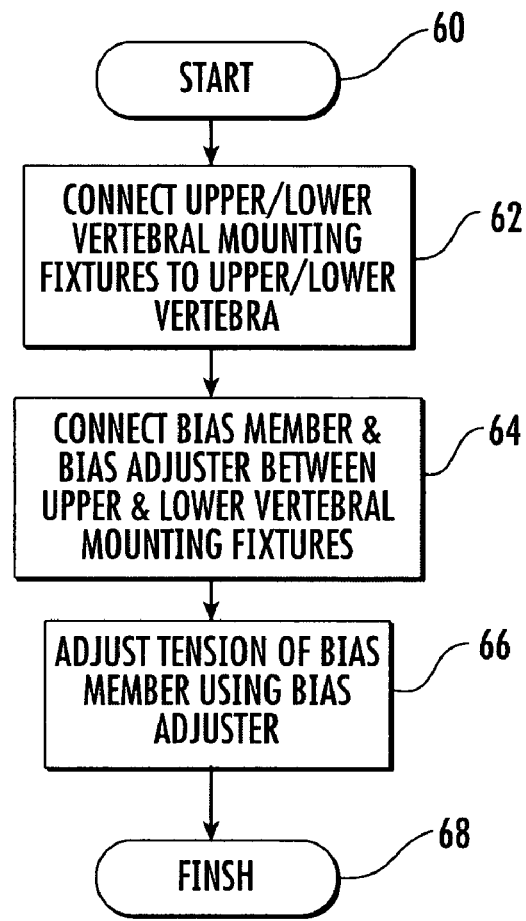
FIGS. 6 and 7 are flow diagrams illustrating methods for providing intervertebral support in accordance with the present invention.

An exemplary method for providing intervertebral support for a patient's spine using the intervertebral support device 20 is now generally described with reference to FIG. 6. The method begins (Block 60) with connecting upper and lower vertebral mounting fixtures 21, 22 each to a respective upper and a lower vertebra in the patient's spine, at Block 62. Further, a bias member 28 and a bias adjuster 29 are connected between the upper and lower vertebral mounting fixtures 21, 22, at Block 64. The bias member 28 may urge the upper and lower vertebral mounting fixtures together 21, 22, as discussed further above. The method further includes adjusting a tension of the bias member 28 using the bias adjuster 29, at Block 66, thus concluding the illustrated method (Block 68).

Figure 7:
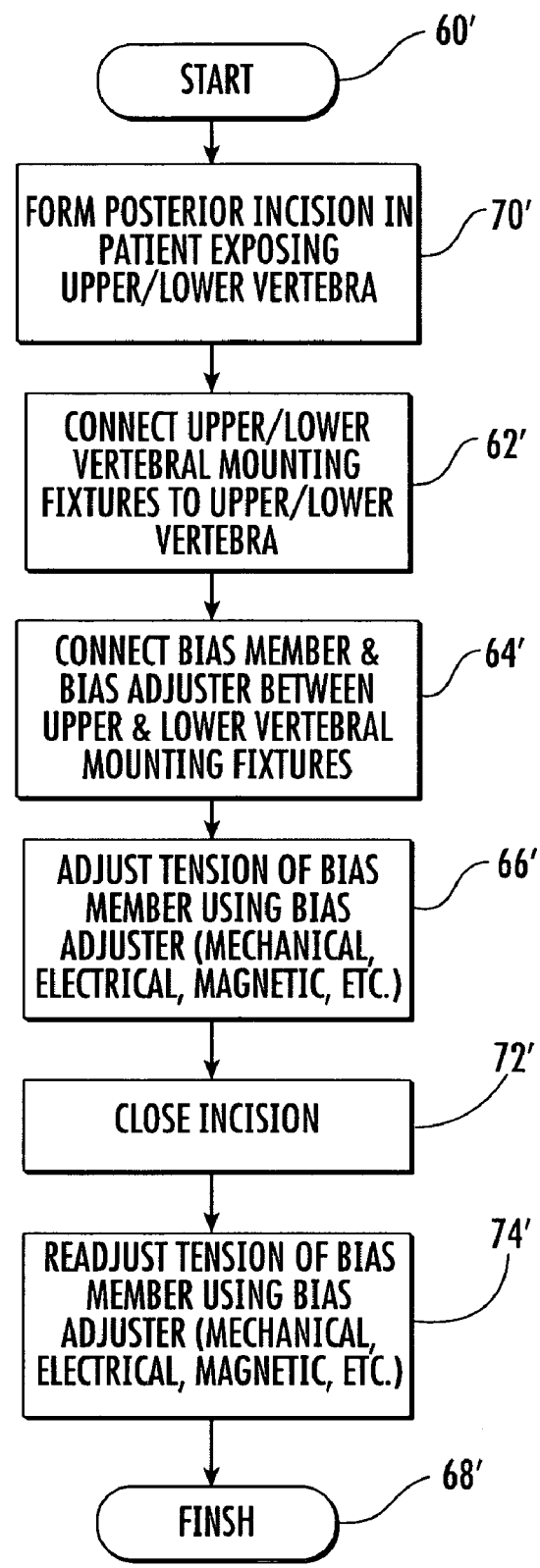

Turning now additionally to FIG. 7, further details regarding the surgical implantation and adjustment of the intervertebral support device 20 are now described. After the patient is readied for surgery, a posterior incision is made in the patient's back 35 to expose the problem disk and the upper/lower vertebra on either side thereof, at Block 70'. The anchors 24 (e.g., pedicle screws) are placed posteriorly into the intervertebral segments through the pedicles 36 through a medialized (i.e., centralized) approach, as opposed to being located on opposite sides of the spine. Stated alternatively, the bias member 28 is connected between the cross-support members 27 and centered between the anchors (i.e., between the detachable locking heads 25), as seen in FIG. 1. As noted above, anchors with holes 26 or openings may be used to provide bone ingrowth and thus a relatively permanent connection.

Because of the fortuitous trajectory of the medialized device, the flexible support member is centralized in the lumbar spine in the position of the posterior spinous processes. This reduces the obstruction of paravertebral musculature, and allows for easy access for mechanical adjustment through a percutaneous approach, as noted above.

The anchor 24 placement is made through the previously described medialized trajectory. The anchor screws may be placed in the pedicles 36 on a substantially permanent basis through the medialized approach utilizing the benefits of bone morphogentic protein (BMP) and "bone putty" to forge a permanent anchor into the vertebral bone above and below a disk segment posteriorly, as will be appreciated by those skilled in the art.

After surgery is completed and the incision is closed, at Block 72', the tension of the bias member 28 may advantageously be re-adjusted at a later time to provide more or less stiffness as necessary, at Bock 74'. Again, this may be done by percutaneous adjustment through local anesthetic and fluoroscopic guidance, or stereotactic guidance of another tool that can adjust the bias adjuster 29 through the percutaneous approach posteriorly. Of course, the other adjustment techniques described above (e.g., electrical actuation, magnetic actuation, physical manipulation) may also be used.

It should also be noted that the support device 20 may advantageously be used in conjunction with an anterior intradiskal device posteriorly to create more motion or less motion, thereby protecting the intradiskal device anteriorly, and allowing more or less motion based on post-operative adjustments. The device 20 may be used in conjunction with more than one disk segment by adding additional flexible support members, tension adjust devices, etc., up and down the spine as needed, as will be appreciated by those skilled in the art.

A specific application to scoliosis surgery will now be further described. In this application, the support device 20 may be placed segmentally through the scoliotic segments. It would also allow for rotation distraction compression while allowing increased motion after correction of the scoliosis, as discussed above. This would advantageously provide the scoliotic patient with correction of the scoliosis through segmental correction while allowing motion of the spine through the spring mechanism.

It should be noted that in some applications there may be a potential for the anchors (i.e., screws) 24 to loosen if the device 20 is engaged or tightened too much at the time of surgery. In such cases, it may be desirable to wait for a period of time before significantly "tightening" the device 20 with the bias adjuster 29 to allow for bony ingrowth and stabilization of the bone-anchor interface. By way of example, this may take about six to eight weeks. Once the bone is strong around the anchors 24 then the device 20 may be adjusted using one of the above-described bias adjustment techniques.

For some patients it may be possible to utilize the principle of "Wolfs Law," which teaches that a relatively small amount of stress to the bone from the anchor 24 may actually increase the bone apposition around the anchor to thereby increase the hold of the anchor in the bone. In such cases, a desired amount of tension would be used to stimulate this effect and then "titrate" up the tension of the bias member 28 until the desired benefit of movement of the problem disk is obtained without causing pain.

If long-term loosening of the anchor-bone interface is avoided, then further operations would advantageously not be required to re-anchor the device 20. Moreover, components of the device 20 (e.g., bias member 28, bias adjuster 29, etc.) may be relatively easily replaced at a later time if they break or if new components are available. That is, since the anchors 24 are already in place, a much less invasive procedure may be used to replace such components than would be required to replace the anchors as well, as will be appreciated by those skilled in the art.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An intervertebral support device comprising:
   upper and lower vertebral mounting fixtures to be respectively connected to an upper and a lower vertebra in a patient's spine;
   a bias member maintained in tension for urging said upper and lower vertebral mounting fixtures together; and
   a bias adjuster connected to said bias member for increasing the tension thereof to allow less vertebral movement and for reducing the tension thereof to allow greater vertebral movement;
   said upper and lower vertebral mounting fixtures each comprising a respective anchor to be connected to each vertebral pedicle, and a respective cross-support member connected between said anchors;
   said bias member being connected between said cross-support members and centered between said anchors to be centrally positioned over a midline of the spine along the spinous processes thereof.

2. The intervertebral support device of claim 1 wherein said bias adjuster is mechanically actuatable with a tool.

3. The intervertebral support device of claim 1 wherein said bias adjuster is electrically actuatable.

4. The intervertebral support device of claim 3 wherein said bias adjuster is inductively powered.

5. The intervertebral support device of claim 1 wherein said bias adjuster is magnetically actuatable.

6. The intervertebral support device of claim 1 wherein said bias member comprises a spring.

7. The intervertebral support device of claim 1 wherein said anchors comprise pedicle screws.

8. An intervertebral support device comprising:
   upper and lower vertebral mounting fixtures to be respectively connected to an upper and a lower vertebra in a patient's spine and each comprising
   a respective anchor to be connected to each vertebral pedicle, and
   a respective cross-support member connected between said anchors;
   a spring maintained in tension for urging said upper and lower vertebral mounting fixtures together and connected between said cross-support members and centered between said anchors; and
   a bias adjuster connected to said spring for increasing the tension thereof to allow less vertebral movement and for reducing the tension thereof to allow greater vertebral movement;
   said spring being connected between said cross-support members and centered between said anchors to be centrally positioned over a midline of the spine along the spinous processes thereof.

9. The intervertebral support device of claim 8 wherein said bias adjuster is mechanically actuatable with a tool.

10. The intervertebral support device of claim 8 wherein said bias adjuster is electrically actuatable.

11. The intervertebral support device of claim 8 wherein said bias adjuster is magnetically actuatable.

12. The intervertebral support device of claim 8 wherein said anchors comprise pedicle screws.

* * * * *